(12) United States Patent
Heinrich et al.

(10) Patent No.: US 10,058,272 B2
(45) Date of Patent: Aug. 28, 2018

(54) SLEEP MONITORING SYSTEM AND METHOD

(71) Applicant: KONINKLIJKE PHILIPS N.V., Eindhoven (NL)

(72) Inventors: Adrienne Heinrich, Eindhoven (NL); Henriette Christine Van Vugt, Eindhoven (NL); Vincent Jeanne, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 7 days.

(21) Appl. No.: 15/101,433

(22) PCT Filed: Dec. 4, 2014

(86) PCT No.: PCT/EP2014/076476
§ 371 (c)(1),
(2) Date: Jun. 3, 2016

(87) PCT Pub. No.: WO2015/086414
PCT Pub. Date: Jun. 18, 2015

(65) Prior Publication Data
US 2016/0310046 A1    Oct. 27, 2016

(30) Foreign Application Priority Data
Dec. 13, 2013 (EP) .................................. 13197190

(51) Int. Cl.
*A61B 5/08*  (2006.01)
*A61B 5/11*  (2006.01)
(Continued)

(52) U.S. Cl.
CPC .......... *A61B 5/1128* (2013.01); *A61B 5/0077* (2013.01); *A61B 5/113* (2013.01);
(Continued)

(58) Field of Classification Search
CPC .... A61B 5/1116; A61B 5/1128; A61B 5/4806
See application file for complete search history.

(56) References Cited

U.S. PATENT DOCUMENTS 5,846,086 A * 12/1998 Bizzi et al. ........ A63B 24/0006
434/247
8,542,877 B2  9/2013 Jeanne
(Continued)

FOREIGN PATENT DOCUMENTS

WO   2012131589 A2   10/2012

OTHER PUBLICATIONS

Adrienne Heinrich et al: "Lifestyle Applications From Sleep Research" Journal of Ambient Intelligence and Humanized Computing, vol. 5, No. 6, Apr. 22, 2014, pp. 829-842.
(Continued)

*Primary Examiner* — Michael D Abreu

(57) ABSTRACT

The sleep monitoring system uses a motion vector estimator to determine motion vectors as a function of location in camera images. A signal processing system with an input coupled to the motion vector estimator computes a measure of turning motion, by summing motion vectors from respective locations within an image. Pose changes are detected based on the measure of turning motion. The measure of turning motion may be computed from a sum of components of the motion vectors that are normal to the major axis of a body area in the image, which is determined based on image content changes in a set of images from the camera. To avoid false turning detection due to leg kicking or similar motion the detected turning motion may be reduced to zero if it is not detected in a sufficiently large part of the body area.

12 Claims, 4 Drawing Sheets

(51) Int. Cl.
    *A61B 5/113* (2006.01)
    *A61B 5/00* (2006.01)
    *A61B 5/1171* (2016.01)

(52) U.S. Cl.
    CPC .......... *A61B 5/1116* (2013.01); *A61B 5/1176* (2013.01); *A61B 5/4806* (2013.01); *A61B 5/4818* (2013.01); *A61B 5/746* (2013.01); *A61B 2503/04* (2013.01)

(56) References Cited

U.S. PATENT DOCUMENTS

| | | | |
|---|---|---|---|
| 8,542,878 B2 | 9/2013 | Cennini | |
| 8,553,940 B2 | 10/2013 | Kirenko | |
| 2006/0001545 A1* | 1/2006 | Wolf | A47K 3/001 340/573.1 |
| 2006/0050930 A1 | 3/2006 | Szuba | |
| 2007/0136102 A1* | 6/2007 | Rodgers | A61B 5/1113 705/3 |
| 2007/0156060 A1* | 7/2007 | Cervantes | A61B 5/1128 600/534 |
| 2009/0182248 A1 | 7/2009 | Jensen | |
| 2010/0331630 A1 | 12/2010 | Odio | |
| 2013/0182107 A1 | 7/2013 | Anderson | |
| 2013/0215248 A1 | 8/2013 | Ishii | |

OTHER PUBLICATIONS

Adrienne Heinrich et al "Body Movement Analysis During Slieep Based on Video Motion Estimation", 2013 IEEE 15th International Conf. on E-Health Networking, Applications and Services (HEALTHCOM2013), Oct. 9, 2013, pp. 539-541.

I G. De Haan, P.W.A.C. Biezen, H Huijgen, O.A. Ojo, "True-motion estimation with 3-D recursive search block matching", IEEE, IEEE Transactions on Circuits and Systems for Video Technology, vol. 3, No. 5, pp. 368-379, Oct. 1993.

G. De Haan, P. Biezen, "An Efficient True-Motion Estimator Using Candidate Vectors from a Parametric Motion Models", IEEE Transactions on Circuits and Systems for Video Technology, vol. 8, No. 1, Feb. 1998.

J.C.Greiner, J.C., S. Ramanathan, J.L. Van Meergergen, G. De Haan, "Object Based Motion Estimation: A Cost Effective Implementation". pp. 1-6.

Evelyn B. Thoman and W.Douglas Tynana, "Sleep states and wakefulness in human infants: Profiles from motility monitoring", Physiology & Behavior, vol. 23, Issue 3, Sep. 1979, pp. 519-525.

A. Sadeh, L. Tikotzky, A. Scher (2010).Parenting and infant sleep. Sleep Medicine Reviews 14: 89-96.

P. Violoa et al, Rapid Object Detection using a Boosted Cascade of Simple Features, CVPR 2001.

* cited by examiner

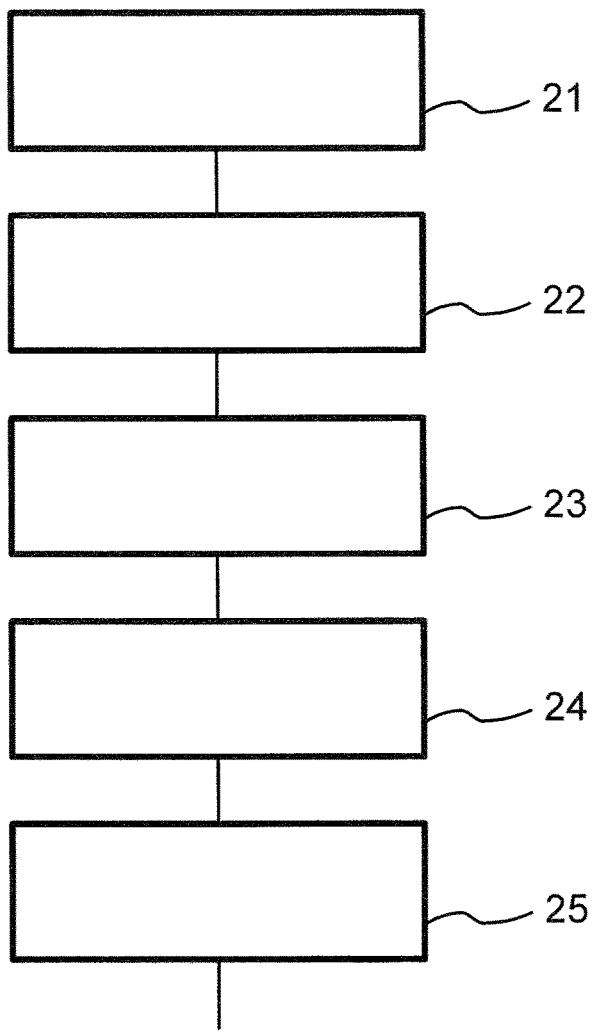
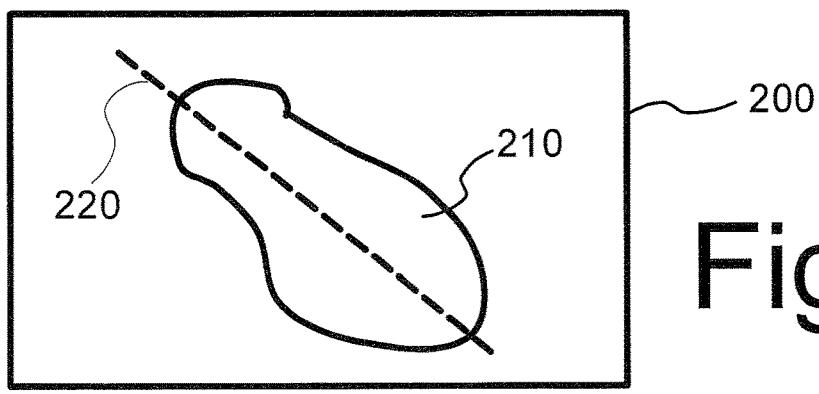

SLEEP MONITORING SYSTEM AND METHOD

This application is the U.S. National Phase application under 35 U.S.C. § 371 of International Application No. PCT/EP2014/076476, filed on Dec. 4, 2014, which claims the benefit of International Application No. 13197190.5 filed on Dec. 13, 2013. These applications are hereby incorporated by reference herein.

FIELD OF THE INVENTION

The invention relates to a monitoring system for monitoring a sleeping person, such as a baby. The invention relates to an automated monitoring method.

BACKGROUND TO THE INVENTION

US20070156060 discloses a real time video based automated mobile sleep monitoring system. A processor infers real-time information about the sleeping state of a subject from the video images, distinguishing between sleeping states. For adults, sleeping states like deep sleep, low rhythm breathing, abnormal movement, obstructive apnea and central apnea can be used as distinguishable sleeping states. US20070156060 discloses that the monitoring system can also be applied to a baby monitor. For infants states like sleeping, awake, standing up, lying on back, lying on stomach, moving, occasionally turning over, crying, thrashing and vomiting can be used as distinguishable states. The system may generate different sleep reports for adults or infants. But the detection operation is described in general without addressing problems that are particular to baby monitoring.

It is known to use image data correlation to determine the state of a subject. US20070156060 uses correlation between image content changes to determine sleeping state. A frame comparator compares pixel values between a pair of images obtained one second from each other. When the difference between image gradients at corresponding locations in images obtained at a pair of time points exceeds a threshold, motion is detected. This results in a map of image locations where motion has been detected for the pair of time points. The processor computes correlations between maps for different pairs of time points. The correlations are used to detect whether there is a temporally repetitive pattern. The detection results are used as an indication of sleep state.

Even though such techniques can provide some information, it remains a problem to increase the robustness and reliability of the determination of sleeping state. For babies in particular, detected motion is often not associated with turning: babies often make large movements with their arms and legs. Furthermore, babies move around during sleep far more than adults, who basically remain aligned with the length of the bed.

SUMMARY TO THE INVENTION

Among others, it is an object to provide for a monitoring method and system for monitoring persons, such as babies, while sleeping on a bed, wherein a more reliable determination of sleeping state is possible.

A monitoring system according to claim 1 is provided. Herein motion vectors are used to obtain a measure of turning motion. Motion vector estimation is known per se for example from MPEG video encoding. By using a sum of motion vectors detected for different blocks in an image a more reliable measure of turning motion can be realized. A sum of motion vectors can also be used to detect movement due to breathing, from which a state associated with a sleeping pose can be determined. Detection of a predetermined state, and/or persistence of the same detected state for more than a predetermined amount of time can be used to generate an alert signal to a user.

In an embodiment, a sum of the components of motion vectors in a direction normal to a major axis of a body area in the image is used in the computation of the measure of turning motion. This facilitates distinction from non-turning motion. In a further embodiment, the body area is determined based on image content changes in a set of images from the camera, captured during a time window including a time point of capturing said image or adjacent to said time point. It has been found that in the case of babies in particular the major axis of the body area can deviate significantly from the longitudinal direction of the bed. By adapting the major axis based on image change data the measurement of turning motion can be made more reliable. The detected body area may be used to select a region of interest in images from the camera for breathing detection, face detection and or heart beat detection dependent on a direction of the major axis.

In an embodiment the signal processing system is configured to detect quiescent time intervals wherein the measure of turning motion indicates less than a predetermined amount of motion; assign different pose states to successive ones of the detected time intervals each based on signs of the measure of turning motion in further time intervals surrounding the time interval, and/or on a position of the time interval in a sequence of time intervals in which the detected time intervals occur.

Thus for example different pose states may be assigned quiescent time intervals according to whether the sign of the motion in surrounding time intervals of turning motion indicates that the quiescent time interval is a local maxima and minima of an accumulated measure of turning motion respectively. An "on the belly" pose state may be assigned to a quiescent time interval if the preceding quiescent time interval was assigned to an "on the back state" and so on. Separate quiescent time intervals containing a local maximum/minimum may be detected as time intervals that are separated from other quiescent time intervals by intervals of turning motion wherein more than a threshold amount of measured turning motion occurs, optionally at least during a predetermined amount of time.

In an embodiment the pose states include an on the belly pose state, an on the back pose state and an on the side pose state. In this embodiment accumulated sizes of the measure of turning motion between quiescent time intervals and/or the detected duration of the turning motion between the quiescent time intervals may be used to select between assigning different pose states. In an embodiment a sign of the measure of turning motion between the quiescent time intervals to select between using transitions to an on the left side pose state and an on the right side pose state.

In an embodiment the signal processing system is configured to perform face detection and/or breathing detection based on images from the camera and to set part of the assigned pose states based on results of face detection and/or breathing detection. In this way an ambiguity, corresponding to swapping on the back and on the belly pose states in a sequence of quiescent time intervals, can be eliminated. In an alternative embodiment ambiguity may be eliminated by using user input that specifies the state in a quiescent time interval.

In an embodiment the signal processing system generates an alert signal when a predetermined pose state like "on the belly" has been assigned, for example subject to a condition that this state has persisted more than a predetermined amount of time. This can be used to warn for a risk of sudden infant death syndrome. Optionally, the signal processing system is configured to generate the alert signal when it has detected a change have a measured breathing parameter and persistence of the predetermined pose state. Similarly an alarm may be generated when the same pose state remains assigned for a second predetermined time interval to warn for a risk of flat head syndrome. The duration of the second time interval may be longer than that of the time interval used to warn for the risk of sudden infant death. In other embodiments state statistics may be collected and reported for use in sleep evaluation.

In an embodiment the determination of the measure of turning motion comprises detection whether motion vectors in at least a predetermined fraction of the image locations in the body area or a part thereof exceed a threshold size and, if not, decreasing the measure of turning motion. Lack of motion in a sufficient fraction of the body area indicates that the motion may be due to leg kicking rather than turning. Thus, detection of motion unrelated to turning can be disabled. The measure of turning motion may be reduced to zero for example if a sufficient fraction of the body area does not show motion. In a further embodiment, the measure of turning motion is decreased when sufficient motion is not detected in respective areas. Thus a test in an area that does not show the baby's legs can be included.

In an embodiment the measure of turning motion is determined by accumulating sums of motion vectors from respective locations as a function of time, optionally after replacing the sums by zero or another reduced value for time points where motion has not been detected in a sufficiently large area, and low pass filtering the accumulated sums. It has been found that this yields reliable turning detection results.

The method may be implemented using a computer program on a computer program product such as a tangible medium like a magnetic or optical disc or a semi-conductor memory.

BRIEF DESCRIPTION OF THE DRAWING

These and other objects and advantageous aspects will become apparent from a description of exemplary embodiments with reference to the following figures.

FIG. 2 shows a flow-chart of body position detection
FIG. 2a shows a map including a body area and a major axis of the body area

DETAILED DESCRIPTION OF EXEMPLARY EMBODIMENTS

Figure 1:
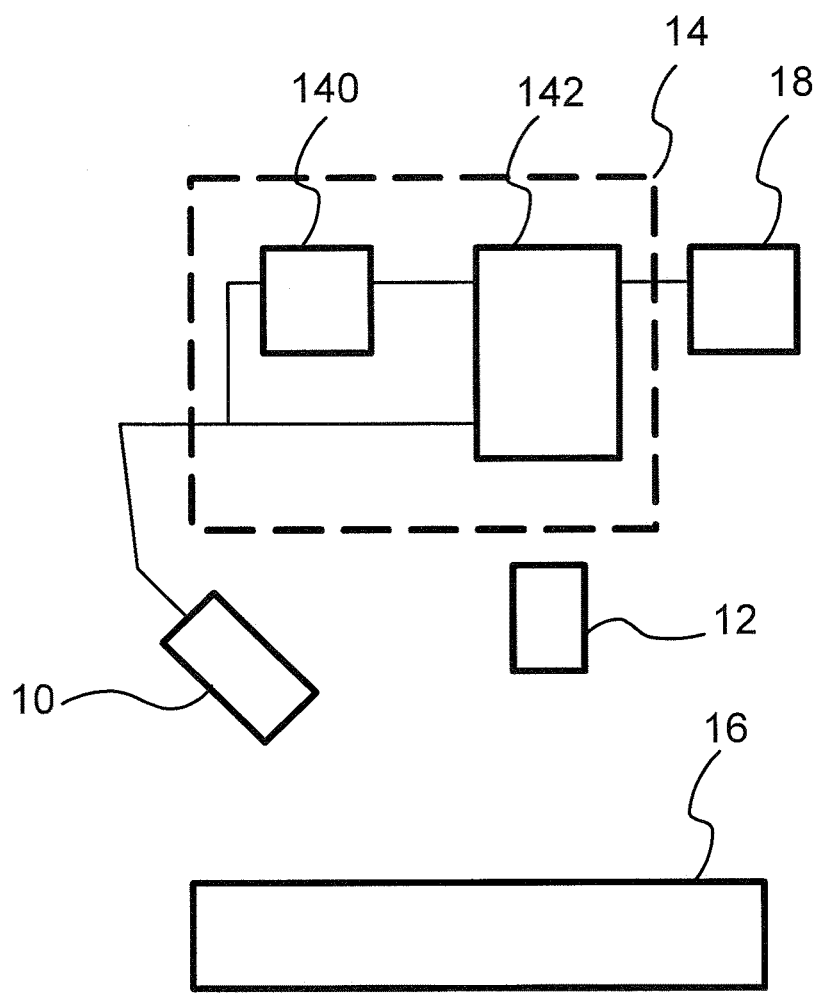
FIG. 1 shows a monitoring system

FIG. 1 shows a monitoring system comprising a camera 10, an optional light source 12, an optional transmitter 18 and a signal processing system 14 comprising a motion vector estimator 140 and an evaluation module 142. In operation, camera 10 and optionally light source 12 are directed at a sleeping surface of a bed 16, to capture successive images of a person on the sleeping surface. Evaluation module 142 may be configured to generate an alert signal and/or optionally cause transmitter 18 to transmit an alert message when it detects from the camera images that the person on the sleeping surface is in an undesirable position, for example when the person is on its belly. When the person is an infant, this may be used to intervene to reduce the risk of sudden infant death (SID). Evaluation module 142 may be configured to compute statistics of body positions, such as the frequency of turning and average duration that the person is in respective positions.

In such a monitoring system the reliability of detection of body motion and/or body position is an important feature. Effectiveness of the system declines with increased frequency of failure to detect undesirable positions. Frequent false alarms increase the risk that alerts will not be followed up.

FIG. 2 shows a flow chart of body rotation detection. The flow chart is executed repetitively for images obtained at successive time points. In a first step 21 signal processing system 14 receives an image from camera 10. In a second step 22 motion vector estimator 140 determines motion vectors for respective blocks of image locations.

In a third step 23 evaluation module 142 uses the received image and/or the motion vectors to update a map of locations in the image that are associated with a body area of a person in the image, or at least a map of an outline of a set of such locations. In a fourth step 24 evaluation module 142 uses the map of locations in the image that are associated with the body area to determine the direction of a major axis of the body area (cf. FIG. 2a).

In a fifth step 25 evaluation module 142 computes a sum of the normal motion vector component detected in the respective blocks in the image in a direction perpendicular to the major axis of the body area. From fifth step 25 the process repeats from first step 21 for a next image captured at a next time point. In this way, the sum values obtained in successive executions of fifth step 25 are obtained as a function of time. Sums of the normal motion vector components may be computed for each captured image (e.g. at a 50 or 60 Hz frame rate), but it may suffice to do so for a sub-sampled set of images, e.g. using one image every 0.1 second or even less frequent images. This reduces the required amount of processing. The sum of the normal motion vector component may be used directly as a measure of turning motion.

Optionally, evaluation module 142 may perform a sixth step wherein it adds the sum to an accumulated sum of normal motion vectors. In this way, the accumulated sum values obtained in successive executions of sixth step 26 are obtained as a function of time.

Figure 3:
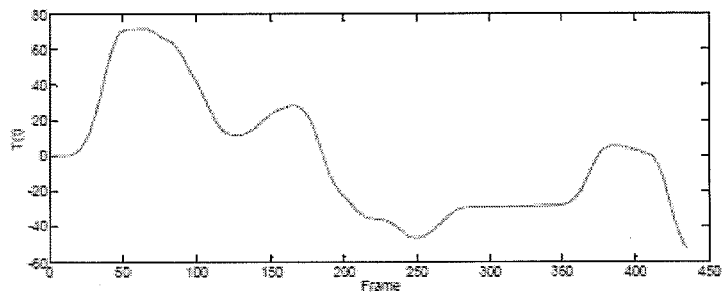
FIG. 3 shows a plot of accumulated sums of normal motion vectors

FIG. 3 shows an example of a smoothed plot of the accumulated sum values of normal motion as a function of time obtained from images of a baby. In those time ranges where the slope is large, the observed person turns. Between these turning time ranges there are quiescent time ranges that included local minima and maxima. In the quiescent time ranges the body of the observed person is in a fixed pose, e.g. on its back or on its belly. For example local maxima may all correspond to an on the belly pose and the local minima may all correspond to an on the back pose.

Smoothing may be realized by temporal low pass filtering, such as averaging the accumulated value over a predetermined number of successive time points (e.g. five time points). The accumulated sum values and their low pass filtered version or its time derivative may be used as a measure of turning motion instead of using the sum of the normal motion directly as a measure of turning motion.

Fourth step 24 may be replaced by use of a preset direction when a measure of turning motion is computed for adults. In this case determination of the direction of the major axis may be replaced by use of a direction that corresponds to the main direction of the bed (from the head end to the foot end). However, it has been found that for monitoring sleeping pose of small children determination of the direction of a major axis of the body is needed, as small children exhibit considerable motion that is unrelated to turning and they can assume widely varying orientations relative to the bed.

In a further embodiment a test step is performed wherein a first count is computed of image location blocks wherein a motion vector above a predetermined motion vector threshold (e.g. zero) has been detected. Furthermore, a second count is computed of image location blocks that lie in an upper part of the body area indicated by the map of locations. Herein the upper part may be selected as a region of image points whose projection on the major axis lies beyond a selected point on the major axis, using a selected point on the major axis that lies at least halfway the length of the body along the major axis, and more preferably no more than 40 percent of the length from the head end of the major axis. In an embodiment, only those locations are counted whose motion vector projection on the normal of the major axis exceed the predetermined motion vector threshold. When the first and second count do not exceed predetermined first and second threshold respectively, the size of the sum value of the normal motion vectors is replaced by zero. Alternatively the sum value may be decreased by a factor. Preferably, the test step is performed before fifth step 25 and the computation of fifth step 25 is skipped when the first and second count do not exceed predetermined first and second threshold respectively. But alternatively, fifth step 25 may be performed in any case. Thus, instead of using the sum of normal motion directly as a measure of turning motion, a function of time wherein the sum has been reduced or replaced by zero dependent on the test step may be used as a measure of turning motion. Use of zero with and without computation of the sum and decreasing by a factor will all be referred to as decreasing the measure of turning motion.

Addition of the test step has the advantage that rotation detection can be disabled when motion vectors are not due to whole body rotation but only to local motion. Babies in particular tend to produce motion like leg kicking that does not correspond to rotation. By using the test step, the risk of false rotation detection due to such movement can be reduced.

The motion vector detection of second step 22 may be performed using methods that are known per se. Methods are known per se for example from video encoding (e.g. MPEG) or from picture rate conversion algorithms wherein 'true' motion is an important characteristic. For example, for each respective block in an array of 8×8 pixel blocks in the image, motion vector estimator 140 may search among 8×8 pixel source block in a previously received image to identify which source block has an image content differs least from that of the respective block. The motion vector for the respective block may be determined from the difference between the location of the respective block and the identified source block.

FIG. 2a shows an example of a body area 210 within a map 200 of locations within an image that are associated with the body area. Line 220 indicates the major axis of body area 210. The updating of third step 23 of the map of locations in the image that are associated with a body area of a person in the image may be based on detection of local image content changes and or motion vector size. Respective locations may be marked when the change of image content associated with the respective location has exceeded a threshold at any time during a time interval of predetermined length prior to capturing the image, for example during at least half a second and no more than one minute.

In an embodiment a motion history image may be used, wherein each of a set of image locations is associated with a time value of a last time point at which an image content change was detected for the image location (or a null value if no image content change was detected or no detection occurred within a preceding time interval of predetermined length). In this embodiment, third step 23 may comprise comparing local image content for the image location in the current image and a previous image, and updating the time value for the image location to the current time when more than a predetermined amount of change was detected. In this case, the body area for the current time point may be taken to be an area containing image locations at which the time value is not more than a predetermined temporal distance in the past.

As image content associated with the respective location, a pixel value at the respective location may be used, or the content of a block of pixel values at predetermined spatial locations relative to the respective location. The motion vectors for respective location may be used as a detection of the change of image content for example.

A major axis of the body area corresponds to a line that runs through the body area, in a direction selected so that a size of the body area along that direction is larger than the size in at least half, and more preferably at least two thirds percent of all possible directions. Preferably the line is located so that it divides the body area into equal sized parts. Preferably a major axis in a direction is used wherein the size of the body area along that direction is larger than the size in all other directions, or at least not smaller. When such a preferred major axis is used, a transverse motion component transverse to this preferred major axis may be used instead of the normal motion, wherein transverse means not parallel, preferably between ninety plus or minus forty five degrees to the preferred major axis and more preferably ninety plus or minus thirty degrees.

Any one of various methods of determining a major axis may be used. The determination of the direction of the major axis of the body area may be performed for example by least square fitting a line to the image locations that lie in the body area according to the image map, or to image locations on the boundary of the body area. A computation of moments may be used (average linear x, y image location values and average bilinear values $Rxx=(x-<x>)*(x-<x>)$, $Rxy=(x-<x>)*(y-<y>)$, $Ryy=(y-<y>)*(y-<y>)$). In this case the major axis may be determined as an eigenvector of the matrix $((Rxx, Rxy), (Rxy,Ryy))$ and selecting that eigenvector that has the largest eigenvalue. Alternatively, the size along a plurality of directions may be determined and a direction that yields largest size may be selected.

The computation of the sum in fifth step 25 may be performed by using direction of the major axis and x and y components of the motion vector of each block to compute the component of the motion vector perpendicular to the major axis, and subsequently summing these components over the blocks. Alternatively, the x and y components of the motion vector of the blocks may be summed and the component of the motion vector perpendicular to the major axis may be computed from that sum.

In the accumulated measure of turning motion (smoothed accumulated sum values of normal motion, optionally with a decrease of the sum at time points where the test step does not reveal whole body motion), local maxima and minima can be associated with distinct body poses in general terms. In the example of FIG. 3, the person was on its belly at the time of each local maximum and on its back at the time of each local minimum.

FIG. 3 illustrates that local maxima and minima in the smoothed plot of the accumulated sum values of normal motion. In an embodiment, evaluation module 142 is configured to detect quiescent time interval from the measure of turning motion and to associate quiescent time intervals with states associated with body poses. Dependent on the state and/or its duration an alert signal may be generated, for example when a state with an "on the belly" pose has been selected.

Quiescent time intervals may be detected for example if the turning motion accumulated in the interval is below a predetermined threshold. Evaluation module 142 may be configured to associate a state to each quiescent interval according to the motion direction in the surrounding time intervals of turning motion before and after the quiescent interval. A first state is associated when the preceding turning interval has motion in a first direction and the following turning interval has motion in a second direction opposite to the first direction. Vice versa, the quiescent interval may be associated with a second state if the preceding and following turning intervals have motion in the second and first direction respectively. Herein having a direction of motion may be determined from an accumulated motion in the turning time interval for example. When the surrounding time intervals of a quiescent time interval have the same direction of motion, turn through has occurred and the state of that quiescent time interval may be selected as the opposite of a next or previous quiescent time interval.

However, the relation between states according to local maxima and minima on one hand and distinct body poses on the other hand is not unambiguous: at some occasions the relation may reverse. In an embodiment, the system may be configured to use a user input indicating the true pose at a given time to associate that pose with the one of a local minimum or maximum, that is detected for that time. The system may be configured to require this user input to activate the system after laying the baby on the bed, and/or when it was not yet able to establish an association between pose and of local minima or maxima. In an embodiment the system may be configured to prompt the user for this input, for example when the baby is laid down, or when it was not yet able to establish an association between pose and of local minima or maxima.

Additionally, or in another embodiment, computer implemented visual face detection and/or breathing detection may be used to disambiguate the relation between states associated with minima and maxima and different poses.

In principle computer implemented visual face detection can be used to distinguish different poses on its own. When the camera is directed downwards, or in a mainly downward direction towards the sleeping surface of bed 16, detection of a frontal face can be associated with an "on the back" pose and absence of face detection can be associated with an "on the belly" pose. Detection of a side face may also be used. But it has been found that the absence of frontal face detection of a sleeping person, especially of a baby, often is not due an "on the belly" pose. Moreover, false detections occur frequently.

Computer implemented visual face detection is known per se. See for example P. Viola et al, Rapid Object Detection using a Boosted Cascade of Simple Features, CVPR 2001. This publication uses a learning algorithm to select a number of features from a larger set to form an efficient classifier. Furthermore, a cascade of increasingly more complex classifiers is formed, which allows background regions of the image to be quickly discarded. For example, the classifiers for frontal face detection may rely on detection of a combination of features including a pair of similar image regions that correspond to eyes and a further image region, parallel to the line through the eye regions, that corresponds to a mouth, optionally with a detected image region that correspond to a nose in between. Classifiers for side face detection may rely on detection of a combination of features including successive image regions that correspond to a chin, a nose and an eye region, and eyes and an image region that corresponds to an ear.

Figure 4:
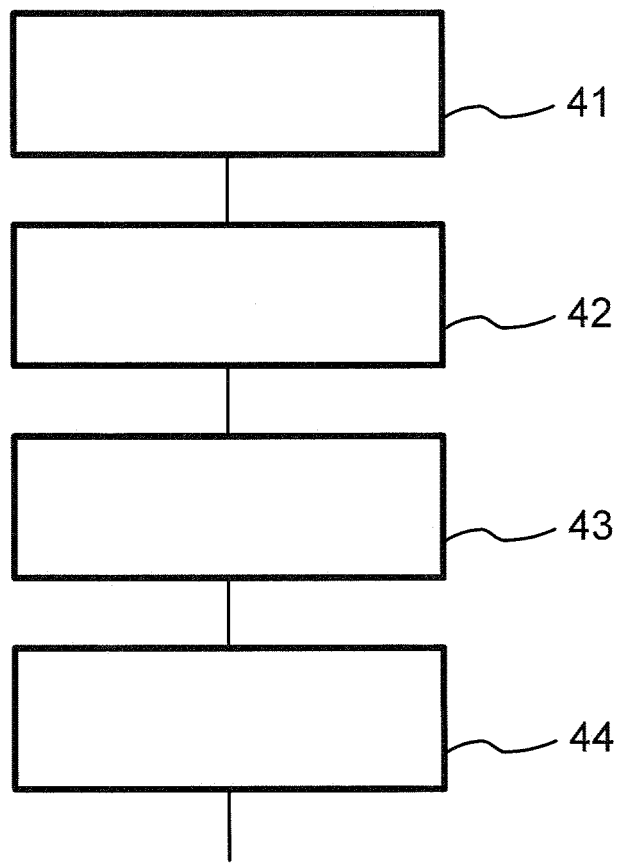
FIG. 4 shows a flow-chart of face detection

FIG. 4 shows a flow chart of face detection based body rotation detection. In a first step 41 evaluation module 142 uses a received image to select regions of interest. In an embodiment evaluation module 142 uses the body area map obtained in the third step 23 of the flow-chart of FIG. 2 for this purpose, by selecting regions at the ends of the detected body area along the major axis.

In a second step 42 evaluation module 142 generates a plurality of differently rotated versions of the image content in the region of interest, using angles that correspond to the direction of the major axis plus predetermined offset angles relative to that major axis. Offset angles in a range of plus or minus fifteen degrees, in steps of three degrees may be used for example.

In a third step 43 evaluation module 142 applies a frontal face detection algorithm and optionally a side face a frontal face detection algorithm to the rotated versions of the image content.

In a fourth step 44 evaluation module 142 sets a face detection result according to whether the face detection algorithm has detected a face in any of the rotated versions or not. Optionally, evaluation module 142 sets a face detection result according to whether a front face, a side face or no face has been detected.

From fourth step 44 the process repeats from first step 41 for a next image captured at a next time point. Thus a face detection result as a function of time is produced.

Figure 5:
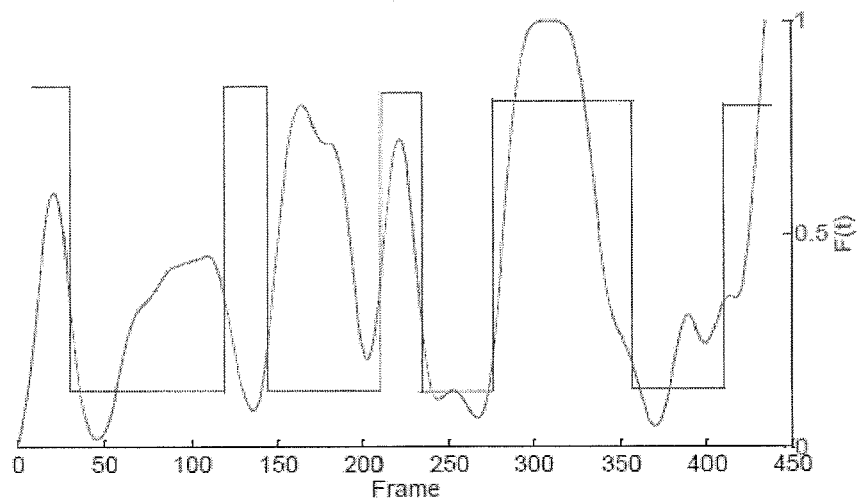
FIG. 5 shows a plot of face detection results

FIG. 5 shows a plot of a smoothed version of the face detection function obtained only with frontal face detection and no frontal face detection results for a baby. Smoothing may be performed by low pass filtering. A high smoothed value indicates that a face was detected at many time points and decreasingly smaller smoothed values indicates that a face was detected less frequently. For reference a rectangular function is shown which indicated whether the observed baby was on its back or not. As can be seen, there is some correlation between an "on the back" position and face detection, but no one to one relation.

However, when combined with detection of turning motion as described using FIG. 2, face detection can be used to disambiguate the results of turning motion detection, i.e. to determine whether a local maximum of the accumulated measure of turning motion correspond to an "on the back" pose or an "on the belly" pose.

Figure 6:
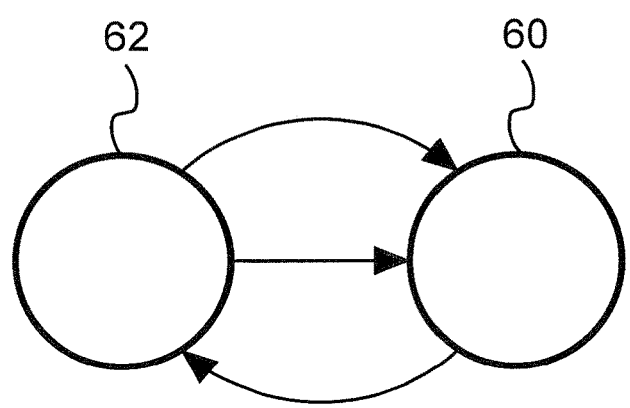
FIG. 6 shows a state model.

FIG. 6 shows a state machine model used in an embodiment to determine pose. The state machine model has states "on the back" 60 and "on the belly" 62. Evaluation module 142 assigns one of these states to successive time points. The assigned state is a copy of the assigned state of the previous time point, unless turning is detected or a face is detected with a threshold reliability. When turning is detected evaluation module 142 changes the state and when a face is detected with a threshold reliability evaluation module 142 sets the state to "on the back". Evaluation module 142 may use the assigned state to compute statistics such as an estimate of the total number of time points that one of the states has been assigned (indicative of the total amount of time spent on the corresponding pose), or the average duration of time intervals wherein the state is assigned between turning).

For this purpose, evaluation module 142 may detect turning by detecting turning time intervals distinguished from quiescent time intervals in the accumulated measure of turning motion. Various methods may be used to detect turning intervals. Time intervals wherein the accumulated measure of turning motion does not deviate by more than a predetermined amount from the maximum or minimum around local maxima or minima, optionally limited to intervals that have at least a predetermined minimum duration, may be considered quiescent time intervals for example. As another example, turning intervals may be identified including time points for which the measure of turning motion (or the time derivative of the accumulated measure of turning motion) exceeds a threshold, or which lie between time points where this occurs, separated by less than a predetermined time distance. Optionally, tests whether the cumulative size of the turning motion in a time interval with motion and/or the duration of that time interval exceed a predetermined threshold or threshold may be used as a condition for identifying the time interval as a turning interval.

Evaluation module 142 may detect whether a face is detected with a threshold reliability if the face detection result indicates a detected face for more than a threshold number of surrounding time points in a time window containing the selected time point. A threshold of ninety percent of the time window may be used for example, and more generally a threshold that reduces the probability of false positive detections below a predetermined threshold, irrespective of the probability of false negatives.

The state machine model of FIG. 6 is only one example. A more complicated state machine model may be used that includes one or more "on the side" states.

When turning is detected evaluation module 142 may determine whether the amount of turning (e.g. an accumulation of the measure of turning motion during the turning interval) and/or its duration is within a predetermined range associated with a full turn or a range associated with a half turn. For example a predetermined threshold may be used to distinguish full turns from half turns. In an embodiment this range is set adaptively, for example using a threshold of three quarter of a maximum detected amount of turning and/or turning duration in detected turning events. As another example using a clustering algorithm to identify clusters of turning events with associated ranges based on the amount and/or duration of turning motion, including full turn and half turn clusters.

Dependent on the result of the determination whether the amount of turning is the full turn rang or the half turn range, evaluation module 142 may select between changing the state by a full turn (e.g. from on the back to on the belly or vice versa) or a half turn (e.g. from on the back to on the side). Furthermore, in an embodiment evaluation module 142 may use the direction of motion (the sign of the measure of turning motion) to select between changing the state in one direction or another (e.g. from on the side to on the belly or to on the back).

Additionally, detection of a side view of a face may be used as an indication of an on the side pose, but this is not certain as the head may be turned sideways when the body is on the belly or on the back. Optionally, when face detection is used, use of detection of a side view of a face is used on condition that this detection starts during or not more than a predetermined time interval after detection of a turning interval from the measure of turning motion.

Although the state machine has been described to express this kind of process, it should be appreciated that evaluation module 142 can implement the process without using an explicit state machine. For example evaluation module 142 may simply set a flag to indicate whether quiescent intervals with minima or maxima of the accumulated measure of turning motion with respect to surrounding turning intervals are associated with an "on the back" pose, and update the flag when a face is detected with a threshold reliability according to whether that detection occurs during a local minimum or local maximum of the accumulated measure of turning motion. Evaluation module 142 may simply select quiescent time intervals around local maxima of the accumulated measure of turning motion, assign an "on the back" pose to such a time interval if a face is detected with a threshold reliability, and otherwise copy the opposite of the pose assigned to a neighboring quiescent time interval.

In further embodiments, signal processing system 14 may comprise a breathing detector and/or a heart beat detector. The breathing detector may be configured to detect breathing from small periodic movement in an image part showing a surface on a torso part of the body. The heart beat detector may be configured to detect heart beats from periodic intensity and/or color variation in an image part showing an exposed part of the body, the variation being due to pulsed blood flow. Techniques for performing visual heart beat detection are disclosed per se in U.S. Pat. No. 8,542,877, U.S. Pat. No. 8,542,878 and U.S. Pat. No. 8,553,940.

The heart beat detector may be configured to use the location of a detected face to select a region of interest, or at least use a region selected according to first step 41. The heart beat detector may sum image intensity values of an image in the selected region. Thus images for successive time points result in a sum of image intensity as a function of time. A temporal autocorrelation or a Fourier transform of this function may be computed and the heart beat frequency may be detected from peaks in the autocorrelation or the Fourier transform amplitude. Optionally, heart beat detection results may be disabled outside quiescent time intervals detected from the measure of turning motion.

The breathing detector may be configured to select a body torso region based on the map of locations in the image that are associated with a body area of a person. Breathing detector may compute a detection function from a motion vector or a sum of motion vectors in the selected region as a function of time. In an embodiment, breathing detector may compute the detection function from a spatial correlation between image content of different images in the selected region as a function of time. Alternatively or in addition motion detection methods where differences between pixel values in (consecutive) images are computed can be used to extract the breathing waveform. From the detection function breathing detector may compute breathing frequency by similar methods as used for heart beat frequency determination.

Light source 12 may be lamp, e.g. comprising a LED. It may be an infrared light source for example. In an embodiment, light source 12 may be configured to project structured light at an angle to the camera viewing direction, for example in the form of a pattern of blocks, or stripes, or an array of rays in respective isolated directions, or in the form of an array of light planes isolated from each other. This can be used to enhance the detectability of breathing motion in the video sequence. Structured lighting may also be used in the detection of turning motion However, it may obstruct heart beat detection.

In a further embodiment light source 12 comprises a structured light source and the monitoring system comprises a control circuit configured to switch the structured light source alternatingly on and off in a periodic pattern, preferably synchronized to image capture by camera 10 so that a first number of the camera images is captured with structured lighting and a second number is captured without structured lighting. In this embodiment the heart beat detector may be configured to operate in synchronism with switching by the control circuit, using only images captured without structured lighting to determine the heart beat frequency. Similarly the breathing detector may be configured to operate in synchronism with switching by the control circuit, using only images captured with structured lighting to determine the breathing frequency.

In an embodiment breathing detection may be used to assist pose detection. In principle computer implemented visual breathing detection can be used to distinguish different poses on its own, because movement due to breathing occurs while the pose remains constant, and the motion pattern differs dependent on pose. Movement due to breathing occurs mainly on the belly and on the chest. When the camera is directed at an angle to the vertical with the major body axis upward-downward in the images observed breathing motion in an "on the back" pose, is mainly upward and downward. In an "on the side" pose, this motion is mainly sideways. Evaluation module 142 may test the direction of observed breathing motion to identify poses accordingly.

Although motion due to breathing is much smaller than that due to turning, the breathing detector may detect it by selectively using image data from parts of the detected body area that are expected to be associated with breathing (the upper part and sides of the body area below the head) and/or making use of the periodicity of breathing movement to band pass filter breathing movements.

In order to detect pose, the location of detected breathing motion and/or its direction of motion may be used. Evaluation module 142 may be configured to evaluate whether the breathing motion is detected over at least a predetermined area within the body area indicated by the map of the body area, and to assign an "on the belly" pose if so. Evaluation module 142 may be configured to evaluate whether the breathing motion is detected mainly in a linear region along the edge of the body area and assign an "on the side" pose if so.

Alternatively, or in addition evaluation module 142 may be configured to distinguish whether a detected breathing motion vector direction is directed more along the major axis of the body area or orthogonally to it, to assign an "on the belly" or an "on the side" pose respectively. Furthermore, evaluation module 142 may be configured to disable breathing detection when the breathing motion amplitude is below a threshold, and or when body turning is detected. Predetermined ranges of areas and/or directions as well as breathing motion amplitude may be defined for evaluation module 142 to use as reference to assign the various poses.

The breathing detector may be configured to detect breathing frequency as described, use the detected breathing frequency to control the central frequency of a band pass filter, and filter detected motion vectors using the band pass filter to obtain a detected breathing motion vector for use in pose detection.

As with pose detection using face detection, pose detection using breathing may suffer from unreliability. Like pose detection using face detection, pose detection using breathing can be used to disambiguate results obtained from the measure of turning motion. For example, when breathing has been detected consistently during at least a predetermined duration, evaluation module 142 may update the state in correspondence with the detected breathing pattern, as described for face detection instead of face detection. In an embodiment, a combination of face detection and breathing detection may be used for this purpose.

Evaluation module 142 may be configured to detect whether the head faces left or right in the "on the side position". The may be determined from face detection and/or breathing direction directly or, if no such detection is available, based on the turning motion. Dependent on whether the measure of turning motion indicates a left motion or right motion in a transition from an "on the back" to an "on the side" pose, evaluation module 142 may mark the on the side state distinctly as left or right facing respectively. Similarly, evaluation module 142 may mark the on the side pose distinctly as left or right facing dependent on whether the measure of turning motion indicates a right motion or left motion respectively in a transition from an "on the belly" to an "on the side" pose.

Based on the detected poses evaluation module 142 may be configured to compute an amount of time that the infant has been lying in each body position overnight a count of turning movements information on head positions and duration per position, time measurements of how long the head of the baby has been in the same position, detection whether the head turned one way most of the time, detection whether the head tilted to one side most of the time.

breathing data, heart rate data, relative amounts of active versus quiet sleep, sleep timing data;

changes in the above factors over time that may be related to development of the baby and development of health risks such as sudden infant death syndrome or flat head syndrome.

Evaluation module 142 may be configured to generate a measurement result image based on one or more of these information items. Based on the detected poses evaluation module 142 may be configured to generate a signal when the baby is lying on the belly and/or when head is lying on the same position longer than a predetermined amount of time.

Evaluation module 142 may be configured to make generation of the signal dependent on results of breathing detection. For example, evaluation module 142 may be configured to generate a signal based on the detected pose conditionally, only when more than a predetermined change in a detected breathing frequency has occurred during in that state, or when no breathing with parameters within a predefined range is detected. This can be used without using breathing detection for pose detection, but a combination with use for pose detection has the advantage that pose detection can be made more reliable without much added overhead.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A monitoring system for monitoring a person on a bed, the system comprising
    a camera for obtaining a set of images of a person on the bed;
    a motion vector estimator with an input coupled to the camera, configured to determine motion vectors as a function of location in each successive image of the set of images obtained during a time interval;
    a signal processing system with an input coupled to the motion vector estimator;
    wherein the signal processing system is configured to
    determine, within each successive image, (i) a map of image locations for blocks in each respective image associated with a body area of the person on the bed and (ii) a direction of a major axis of the body area on the bed from the determined map of image locations, wherein the direction is determined by a size of the body area on the bed along that direction of the major axis being larger than a size of the body area on the bed in all other directions, or at least not smaller, and wherein the direction of the major axis of the body area on the bed is adaptable in response to deviations of the major axis from a longitudinal direction of the bed;
    compute a measure of turning motion of the person on the bed, wherein the computation of the measure of turning motion of the person on the bed comprises (i) using (i)(a) the direction of the major axis of the body area on the bed and (i)(b) components of the determined motion vectors of each block in each respective image that are normal to the direction of the major axis of the body area on the bed and (ii) subsequently summing these components over the blocks from the respective map of image locations associated with the body area of the person on the bed within each successive image of the set of images; and
    detect pose state changes of the person on the bed based on the computed measure of turning motion of the person.

2. The monitoring system according to claim 1, wherein the signal processing system is further configured to
    detect time intervals wherein the measure of turning motion indicates less than a predetermined amount of motion; and
    assign different pose states to successive ones of the detected time intervals, each based on signs of the measure of turning motion in further time intervals surrounding the time interval, and/or on a position of the time interval in a sequence of time intervals in which the detected time intervals occur.

3. The monitoring system according to claim 2, wherein the pose states include an on the belly pose state, an on the back pose state and an on the side pose state, and wherein the signal processing system is configured to use accumulated sizes of the measure of turning motion between the time intervals and/or time duration between the time intervals to select between using direct transitions between the on the belly pose state and the on the back pose state and transitions from the on the belly pose state or the on the back pose state to the on the side pose state.

4. The monitoring system according to claim 3, wherein the signal processing system is further configured to use a sign of the measure of turning motion between the time intervals to select between using transitions to an on the left side pose state and an on the right side pose state.

5. The monitoring system according to claim 2, wherein the signal processing system is further configured to generate an alert signal (i) when a predetermined pose state has been assigned and/or (ii) when a same pose state remains assigned for more than a predetermined time interval.

6. The monitoring system according to claim 5, wherein the signal processing system is further configured to perform breathing detection based on images from the camera and to generate the alert signal on condition that (i) no breathing with parameters within a predetermined range has been detected and/or (ii) a change of detected breathing parameters has been detected, while the predetermined pose state has been assigned.

7. The monitoring system according to claim 2, wherein the signal processing system is further configured to perform face detection and/or breathing detection based on images from the camera and to set part of the assigned pose states based on results of face detection and/or breathing detection.

8. The monitoring system according to claim 1, wherein the signal processing system is further configured to
    determine, within each successive image, the image locations associated with the body area based on image content changes in the set of images from the camera, captured during a time window including a time point of capturing each respective image or adjacent to said time point.

9. The monitoring system according to claim 8, wherein the signal processing system is further configured to select a region of interest in images from the camera for face detection and or heart beat detection dependent on the direction of the major axis.

10. The monitoring system according to claim 1, wherein the signal processing system is further configured to detect whether motion vectors in at least a predetermined fraction of the image locations in the body area or a part thereof exceed a threshold size and, if not, then to decrease the measure of turning motion.

11. The monitoring system according to claim 1, wherein the signal processing system is further configured to detect whether motion vectors in at least a first predetermined fraction of the image locations in the body area exceed a threshold size, and motion vectors in at least a second predetermined fraction of the image locations in a first end part of the body area along the major axis exceed the threshold size and, if not both, then to decrease the measure of turning motion.

12. The monitoring system according to claim 1, wherein the signal processing system is further configured to determine the measure of turning motion by accumulating sums of motion vectors from respective locations as a function of time and low pass filtering the accumulated sums.

* * * * *